US008180016B2

(12) United States Patent
Kanno

(10) Patent No.: US 8,180,016 B2
(45) Date of Patent: May 15, 2012

(54) X-RAY CT APPARATUS AND METHOD THEREOF

(75) Inventor: Ikuo Kanno, Kyoto (JP)

(73) Assignee: Kyoto University (JP)

( * ) Notice: Subject to any disclaimer, the term of this patent is extended or adjusted under 35 U.S.C. 154(b) by 321 days.

(21) Appl. No.: 12/673,197

(22) PCT Filed: Aug. 7, 2008

(86) PCT No.: PCT/JP2008/064229
§ 371 (c)(1),
(2), (4) Date: Feb. 12, 2010

(87) PCT Pub. No.: WO2009/022625
PCT Pub. Date: Feb. 19, 2009

(65) Prior Publication Data
US 2011/0194668 A1    Aug. 11, 2011

(30) Foreign Application Priority Data

Aug. 15, 2007    (JP) .................................. 2007-211948

(51) Int. Cl.
*A61B 6/03* (2006.01)
(52) U.S. Cl. .................................. 378/5; 378/4; 382/131
(58) Field of Classification Search .................. 378/4, 5; 382/131; 600/425, 431
See application file for complete search history.

(56) References Cited

U.S. PATENT DOCUMENTS

| 4,686,695 A | 8/1987 | Macovski |
| 5,533,080 A | 7/1996 | Pelc |
| 5,570,403 A | 10/1996 | Yamazaki et al. |
| 5,953,444 A | 9/1999 | Joseph et al. |
| 6,507,633 B1 | 1/2003 | Elbakri et al. |
| 7,002,158 B2 | 2/2006 | Katagiri et al. |
| 2006/0159223 A1 | 7/2006 | Wu et al. |

FOREIGN PATENT DOCUMENTS

| JP | 2004-223158 | 8/2004 |
| JP | 2004-228482 | 8/2004 |
| JP | 2007-71602 | 3/2007 |

OTHER PUBLICATIONS

Kanno et al., Low Exposure X-ray Transmission Measurements for Contrast Media Detection with Filtered X-rays, 2003, Journal of Nuclear Science and Technology, vol. 40, No. 7, pp. 457-463.*

(Continued)

*Primary Examiner* — Edward Glick
*Assistant Examiner* — John Corbett
(74) *Attorney, Agent, or Firm* — Gerald E. Hespos; Michael J. Porco

(57) ABSTRACT

In an X-ray CT apparatus 1 and an X-ray CT method, the thickness of an object to be inspected is computed on the basis of the number of transmitted X-rays in a specific energy range set above and below the K-absorption edge of an X-ray contrast medium serving as the object to be inspected, and a CT image is reconstructed on the basis of the computed thickness of the object to be inspected. Such X-ray CT apparatus 1 and X-ray CT method can generate an X-ray CT image stably and independently of the size of the object to be inspected and of X-ray tube voltage (X-ray energy distribution).

6 Claims, 13 Drawing Sheets

OTHER PUBLICATIONS

Kanno et al.: "Energy subtraction method with filtered X-rays for the detection of contrast media"—Nuclear Instruments & Methods in Physics Research, vol. 567, No. 1, Nov. 1, 2006, pp. 154-157.

Kanno et al.: "Comparison of current and energy X-ray measurement methods in contrast media detection"—Nuclear Instruments & Methods in Physics Research, vol. 580, No. 1, Aug. 29, 2007, pp. 534-536.

Akio Uesaka et al., "B30 Comparison of Current and Energy Measuremetn Methods of X-rays in Iodine Contrast Media Detection", Atomic Energy Society of Japan '2007 Nen Haru no Nenkai', p. 71.

Ikuo Kanno, "Energy Subtraction Method with Filtered X-rays for Low Dose Radiography", Ionizing Radiation, vol. 32, No. 1, (2006), pp. 49-59.

* cited by examiner x-position (mm)

x-position (mm)

X-RAY CT APPARATUS AND METHOD THEREOF

BACKGROUND OF THE INVENTION

1. Field of the Invention

The present invention relates to an X-ray CT apparatus and an X-ray CT method, and more particularly to an X-ray CT apparatus and an X-ray CT method for generating a CT image based on energy information of transmitted X-rays.

2. Description of the Related Art

Diagnostic imaging based on X-ray transmission imaging or X-ray CT (computed tomography) imaging enables the finding of pathologies such as tumors, ulcers and the like inside a subject, and is therefore used as an effective diagnostic method. In such diagnostic imaging, there is measured the dose of X-rays that pass through a subject (or the dose of X-rays absorbed by a subject). An X-ray image is then generated by graphically representing the measured changes in X-ray dose. The elements present in a living organism are relatively light elements such as hydrogen, nitrogen, oxygen and calcium. The X-ray absorption coefficient of such elements is therefore small. In consequence, the X-ray dose irradiated to the subject must be increased, in order to generate sharp X-ray images, when living organisms are the subjects. This gives rise to the problem of subject exposure.

In Japanese Patent Application Laid-open No. 2004-223158 the inventors have proposed an X-ray imaging method that reduces the exposure of a subject. In Japanese Patent Application Laid-open No. 2007-071602 and Japanese Patent Application Laid-open No. 2004-228482, the inventors have proposed suitable radiation detectors for the above-mentioned X-ray imaging method.

The X-ray imaging method disclosed in Japanese Patent Application Laid-open No. 2004-223158 is an X-ray imaging method for inspecting the interior of a subject using transmitted X-rays that pass through the subject upon irradiation of the latter with X-rays. The method includes a step of evaluating an object to be inspected inside the subject by utilizing information on a specific energy range that corresponds to the object to be inspected, from among energy information of the transmitted X-rays. The X-ray imaging method utilizes thus energy information on transmitted X-rays in a specific energy range. This allows reducing the X-ray dose that is irradiated of the subject, thereby reducing the exposure of the subject.

The radiation detector disclosed Japanese Patent Application Laid-open No. 2007-071602 comprises a plurality of detection media arrayed in the incidence direction of the transmitted X-rays. The energy imparted by the incident transmitted X-rays elicits generation of charge at respective detection media 1, 2, 3 . . . thus numbered sequentially along the incidence direction of the transmitted X-rays. The detection media 1, 2, 3 . . . , however, act also as absorption bodies of the transmitted X-rays. Therefore, the sequence number of the detection media 1, 2, 3 . . . that absorbs the incident transmitted X-rays varies in accordance with the energy of the transmitted X-rays, on account of the dissimilar thickness of the above-mentioned absorption body through which the transmitted X-rays pass until reaching a respective detection medium 1, 2, 3 . . . . That is, low-energy X-rays and low-energy gamma rays are absorbed readily by, for instance, a detection medium 1 and a detection medium 2 on the side where the transmitted X-rays are incident. High-energy X-rays and high-energy gamma rays, by contrast, reach and are absorbed by high-numbering detection media (at positions removed from the incidence end). By measuring the current outputted by the respective detection media 1, 2, 3 . . . , the above phenomenon can be exploited for gathering energy information and, simultaneously, detecting radiation at a high count rate.

The semiconductor radiation detector disclosed in Japanese Patent Application Laid-open No. 2004-228482 is a radiation detector in which there is used a single crystal of a base material InSb, which is a compound semiconductor, and in which there is used a high-purity InSb single crystal not artificially doped with impurities. A semiconductor element, which operates at a predetermined temperature, is thus manufactured in which the high-purity InSb single crystal is imparted with diode characteristics. This semiconductor radiation detector can detect radiation with high energy resolution.

In order to generate a sharp X-ray image in the case where the subject is a living organism it is often necessary to administer a contrast medium having a higher X-ray absorption coefficient, for instance iodine, barium or the like, to the living organism. In such cases, absorption of X-rays by the living organism is not negligible when the X-ray transmission length is substantial on account of the size of the living organism. This reduces the effect of the contrast medium. Greater X-ray doses are ordinarily achieved by raising the voltage applied to an X-ray tube (X-ray tube voltage). Doing so increases the high-energy components in the X-rays that are irradiated onto the living organism. In turn, this reduces the X-rays that are absorbed by the contrast medium.

Japanese Patent Application Laid-open No. 2004-223158 indicates (paragraph [0078]) that the X-ray imaging method disclosed in Patent document 1 (D1) can be employed in CT. The specifics are not disclosed, and the document merely estimates that the elicited effect would entail a reduction in X-ray exposure.

SUMMARY OF THE INVENTION

In the light of the above, it is an object of the present invention to provide an X-ray CT apparatus and an X-ray CT method that allow generating X-ray CT images stably and independently of the size of the subject and of X-ray tube voltage (X-ray energy distribution).

In the X-ray CT apparatus and X-ray CT method according to the present invention, the thickness of an object to be inspected is computed on the basis of the number of transmitted X-rays in specific energy ranges that are set above and below the K-absorption edge of an X-ray contrast medium, and a CT image is reconstructed on the basis of the computed thickness of the object to be inspected. As a result, an X-ray CT apparatus and X-ray CT method such as the above allow generating X-ray CT images stably and independently of the size of the subject and of X-ray tube voltage (X-ray energy distribution).

DETAILED DESCRIPTION OF THE PREFERRED EMBODIMENT

Figure 1:
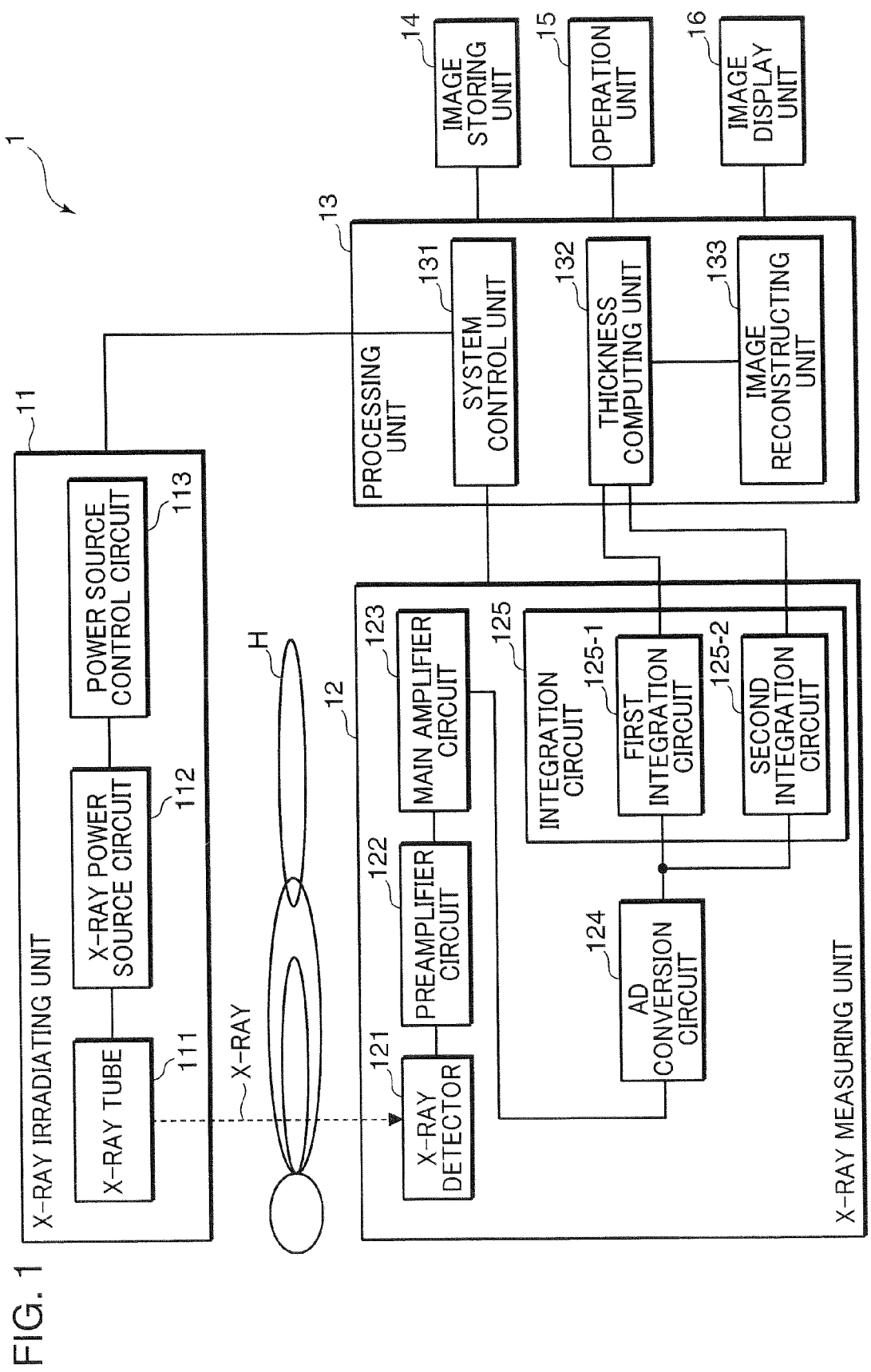
FIG. 1 is a block diagram illustrating the configuration of an X-ray CT apparatus in an embodiment of the present invention.

An embodiment of the present invention is explained next with reference to accompanying drawings. In the figures, identical reference numerals denote identical features, and a recurrent explanation thereof will be omitted.

Features of the Embodiments

FIG. 1 is a block diagram illustrating the configuration of an X-ray CT apparatus in an embodiment of the present invention. In FIG. 1, an X-ray CT apparatus 1 comprises an X-ray irradiating unit 11, an X-ray measuring unit 12, a processing unit 13, an image storing unit 14, an operation unit 15 and an image display unit 16.

The X-ray irradiating unit 11, which is a device that irradiates X-rays, comprises for instance an X-ray tube 111 that generates and radiates X-rays; an X-ray power source circuit 112 that steps up input voltage from a commercial power supply or the like to a predetermined voltage value and supplies the stepped-up voltage power to the X-ray tube 111, to cause the X-ray tube 111 to generate X-rays; and a power source control circuit 113 that controls the X-ray power source circuit 112, in accordance with control by the processing unit 13, so as to control the radiation timing, radiation amount and so forth of the X-rays radiated by the X-ray tube 111. In the X-ray tube 111, power high voltage (X-ray tube voltage) supplied for instance by the X-ray power source circuit 112 is applied between a cathode and an anode. Electrons are emitted thereupon from a filament of the cathode and collide against the anode, as a result of which X-rays are radiated from the X-ray tube 111.

The X-ray measuring unit 12 is disposed so as to oppose the X-ray irradiating unit 11, with a subject H interposed therebetween. The X-ray measuring unit 12 measures the number of transmitted X-rays, from among the transmitted X-rays that pass through the subject H, that lie within a predetermined energy range that depends on the object to be inspected in the subject H. X-rays irradiated by the X-ray irradiating unit 11 onto the subject H strike the X-ray measuring unit 12 via the subject H. That is, the X-rays that pass through the subject H (transmitted X-rays), from among the X-rays irradiated by the X-ray irradiating unit 11, are incident on the X-ray measuring unit 12. The X-ray measuring unit 12 comprises, for instance, an X-ray detector 121 that detects the energy and number of incident X-rays; a preamplifier circuit 122 that amplifies the output of the X-ray detector 121; a main amplifier circuit 123 that further amplifies the output of the preamplifier circuit 122; an analog-digital conversion circuit (AD conversion circuit) 124 that converts the output of the main amplifier circuit 123 from an analog signal to a digital signal; and an integration circuit 125 that integrates the output of the AD conversion circuit 124. The integration circuit 125 comprises a first integration circuit 125-1 that integrates the number of X-rays of an energy region corresponding to a predetermined energy range φ1 that is smaller than the K-absorption edge of the object to be inspected (for instance, an X-ray contrast medium or the like); and a second integration circuit 125-2 that integrates the number of X-rays of an energy region corresponding to a predetermined energy range φ2 that is greater than the K-absorption edge of the object to be inspected. Thus, the integration circuit 125 integrates the number of X-rays in a predetermined energy range set above and below the K-absorption edge of the object to be inspected. That is, the integration circuit 125 integrates the number of X-rays in each predetermined energy range that is set, along the energy axis, above and below the K-absorption edge of the object to be inspected.

For instance, the X-ray measuring unit 12 comprises an X-ray detector 121 that measures incident X-rays in the form of current; a preamplifier circuit 122 that amplifies the output of the X-ray detector 121; an analog-digital conversion circuit (AD conversion circuit) 124 that converts the output of the preamplifier circuit 122 from an analog signal to a digital signal; an energy distribution deriving unit, not shown; and an integration circuit 125 that integrates the output of the energy distribution deriving unit. The X-ray detector 121 has a plurality of detection elements arrayed along the X-ray incidence direction. The current outputted by each detection element is amplified by the preamplifier circuit 122 that is connected to the detection elements, and is digitized by the analog-digital conversion circuit 124. The current values thus digitized are analyzed by the energy distribution deriving unit, which derives therefrom an incident X-ray energy distribution. The integration circuit 125 integrates, by way of the energy distribution deriving unit, the number of X-rays in predetermined energy ranges set above and below the K-absorption edge of the object to be inspected.

Preferably, the X-ray detector 121 can measure energy with a high count rate. The X-ray detector 121 is preferably, for instance, the detector disclosed in Patent document 2 (D2), and comprises for instance a detection medium that generates charge on account of energy imparted by incident X-rays; and a plurality of electrodes disposed in the detection medium at positions removed by mutually different distances from an incidence end of the X-rays on the detection medium. More specifically, the X-ray detector 121 comprises a rectangular silicon substrate extending along the incidence direction of the X-rays; first through fourth electrodes formed on one of the main surfaces of the silicon substrate, along the incidence direction of the X-rays, from the incidence end of the X-rays; and first through fourth diodes respectively connected to the first through fourth electrodes; wherein the silicon substrate is connected to ground. The electrodes are not limited to four and may be a plurality thereof. The material of the X-ray detector 121 is not limited to silicon, and may be, for instance, a semiconductor, CdTe, InSb or a known material used in base materials of radiation detectors such as scintillators. The X-ray detector 121 may comprise a silicon substrate and a plurality of silicon detectors formed by two electrodes that are in turn formed on the front and rear main surfaces of the silicon substrate, so that the silicon detectors are arrayed along the X-ray propagation direction. The X-ray detector 121 comprises a plurality of detection media arrayed in the propagation direction of transmitted X-rays that pass through the subject. Charge is generated at each detection medium on account of energy imparted by the transmitted X-rays, while at the same time the detection media act as absorption bodies of the transmitted X-rays. In the X-ray detector 121, therefore, there varies the thickness of the absorption bodies through which the transmitted X-rays pass before arriving at the respective detection media. The X-ray detector 121 having the above configuration allows measuring the number of transmitted X-rays in a predetermined energy range corresponding to the object to be inspected inside the subject, from among the X-rays having passed through the subject, and a allows drawing a CT image, with the same processing speed as in the case of an X-ray CT apparatus that relies on current measurement. A more practical X-ray CT apparatus 1 can be provided as a result.

For instance, the X-ray detector 121 is preferably the detector disclosed in Patent document 3 (D3). For instance, the X-ray detector 121 is a radiation detector using a single crystal of the compound semiconductor InSb as a base material, wherein the radiation detector has diode characteristics, and an operation temperature ranging from 2 K to 50 K, through formation of a surface barrier layer on an InSb single crystal not artificially doped with impurities. The X-ray detector 121 is also a radiation detector using a single crystal of the compound semiconductor InSb as a base material, wherein the radiation detector has diode characteristics, and an operation temperature ranging from 2 K to 115 K, through formation of a pn junction on an InSb single crystal not artificially doped with impurities. The X-ray detector 121 is also a radiation detector using a single crystal of the compound semiconductor InSb as a base material, wherein the radiation detector has diode characteristics, and an operation temperature ranging from 4.2 K to 115 K, through formation of a pn junction on a p type InSb single crystal resulting from doping an InSb single crystal with Ge.

The X-ray irradiating unit 11 and the X-ray measuring unit 12 are configured so as to rotate and shift, by way of a driving mechanism not shown, relative to the subject H, in order to measure transmitted X-rays of the subject H from all directions, at predetermined angle intervals, so as to generate a CT image of the subject H.

The processing unit 13 controls the entire operation of the X-ray CT apparatus 1 by controlling the various units of the X-ray CT apparatus 1. The processing unit 13 comprises, for instance, a microprocessor and ancillary peripheral circuits. Functionally, the processing unit 13 comprises a system control unit 131, a thickness computing unit 132 and an image reconstructing unit 133.

The system control unit 131 controls the X-ray irradiation operation of the X-ray irradiating unit 11 by exchanging control signals with the X-ray irradiating unit 11, and controls the X-ray measurement operation of the X-ray measuring unit 12 by exchanging control signals with the latter. The X-ray irradiating unit 11, under the control of the system control unit 131, irradiates the subject H with X-rays. The transmitted X-rays that pass through the subject H are measured by the X-ray measuring unit 12, and the resulting measurement output is inputted to the processing unit 13.

The thickness computing unit 132 computes the thickness of the object to be inspected in the subject H on the basis of the number of transmitted X-rays in the above predetermined energy range as measured by the X-ray measuring unit 12.

The image reconstructing unit 133 reconstructs a CT image (CT image data) of the subject H on the basis of the thickness of the object to be inspected as computed by the thickness computing unit 132, in accordance with a predetermined CT imaging method. For instance, the image reconstructing unit 133 uses, as projection data, the thickness of the object to be inspected, which is computed by the thickness computing unit 132, and performs convolution of the projection data and a predetermined reconstruction function. The CT image (CT image data) of the subject H is generated through back-projection of the convolution result. The predetermined reconstruction function (filter) is prepared as a plurality of functions for various clinical purposes, and is appropriately selected in accordance with, for instance, the diagnosis target or the diagnosis site of the subject H.

The image storing unit 14, which stores the CT image (CT image data) generated by the image reconstructing unit 133 of the processing unit 13, is for instance a hard disk device having a comparatively large storage capacity. The image storing unit 14 may also be, for instance, a device for reading and/or writing data to/from a recording medium such as a CD-R (compact disc recordable), a DVD-R (digital versatile disc recordable) or the like. The image storing unit 14 may be, for instance, a CD-R drive or a DVD-R drive.

The operation unit 15 is a device for inputting various operation instructions for operating the X-ray CT apparatus 1.

The image display unit 16 is a device on which there is displayed the CT image generated by the image reconstructing unit 133 of the processing unit 13. This image display unit may be a display device such as a CRT display, an LCD, an organic EL display or a plasma display.

The operation of the present embodiment is explained next.

Embodiment Operation

An appropriate contrast medium is selected from among X-ray contrast media such as an iodine contrast medium, a barium contrast medium or a gold contrast medium, in accordance with the diagnosis target and diagnosis site, and is administered to the subject H. The user inputs then an imaging start instruction by way of the operation unit 15, whereupon the X-ray irradiating unit 11 is controlled by the system control unit 131 of the processing unit 13 to cause the X-ray irradiating unit 11 to irradiate X-rays onto the subject H. The X-ray measuring unit 12 is controlled so that transmitted X-rays that pass through the subject H are measured by the X-ray measuring unit 12. Specifically, upon receiving a control signal from the processing unit 13, the power source control circuit 113 of the X-ray irradiating unit 11 controls the X-ray power source circuit 112 to cause thereby a power of a predetermined voltage to be supplied, at a predetermined timing, to the X-ray tube 111 from the X-ray power source circuit 112, whereupon the X-ray tube 111 irradiates X-rays onto the subject H. The X-rays irradiated onto the subject H pass through the subject H and strike the X-ray measuring unit 12. In the X-ray measuring unit 12, the transmitted X-rays having passed through the subject H strike the X-ray detector 121. The transmitted X-rays are detected by the X-ray detector 121. The detection output from the X-ray detector 121 is amplified by the preamplifier circuit 122 and the main amplifier circuit 123, and is subjected to AD conversion by the AD conversion circuit 124. The converted digital output from the AD conversion circuit 124 is inputted to the first and second integration circuits 125-1, 125-2 of the integration circuit 125. The digital output is integrated by the first and second integration circuits 125-1, 125-2, and is inputted to the processing unit 13.

The above operation is performed while the X-ray irradiating unit 11 and the X-ray measuring unit 12 are displaced by predetermined angle increments relative to the subject H. Transmitted X-ray data of the subject H at predetermined angle intervals in all directions is inputted to the processing unit 13.

To reduce the exposure of the subject H, the X-rays irradiated onto the subject H are preferably filtered X-rays that have passed through a filter comprising, for instance, lanthanum or the like. Passing through the filter causes the intensity of X-rays for a predetermined energy component (for instance, high-energy components in a lanthanum filter) to be attenuated as compared with the intensity of white X-rays. The exposure of the subject H can be reduced as a result.

The thickness computing unit 132 of the processing unit 13 computes the thickness of the object to be detected, such as an X-ray contrast medium in the subject H, based on the transmitted X-ray data. The computation involved is disclosed in, for instance, Patent document 1 (D1) and Patent document 2 (D2), but will be briefly outlined below.

Firstly, the resulting X-ray spectrum $\psi(E)$ after X-rays generated by the X-ray tube have passed through n types of substances is given by formula 1 below, wherein Z is the atomic number of the X-ray tube target, E0(kV) is the X-ray tube voltage, $\mu_i$ is the attenuation coefficient of substance i, $\rho_i$ is the density of substance i, $x_i$ is the thickness of substance i, and c is a constant.

$\psi(E)=c \times Z \times ((E0-E)/E) \times \exp(-\Sigma(\mu i(E)/\rho i)\rho i \times xi)$
(wherein $\Sigma$ is the summation from i=1 to i=n)  (formula 1).

The integration value $\Phi$ of the count number of X-rays within a predetermined energy range is given by formula 2, upon numerical integration based on formula 1.

$\Phi=\Phi 0 \times \exp(-\Sigma ai \times xi)$ (wherein $\Sigma$ is the summation from i=1 to i=n)  (formula 2).

Herein, $\Phi 0$ is the integration value when the thickness of all transmission substances i is 0, i.e. the integration value of the count number of white X-rays within the integration range, and ai is a constant that depends on the integration range and on the substance i.

A system of n equations is thus obtained for m types of substances in the subject H over n integration ranges. An X-ray contrast medium is administered to the subject H, such that in cases where the subject H is a living organism, the X-rays passing through the subject H are mainly absorbed by water, which is abundant in the living organism, and by the X-ray contrast medium. The X-rays become attenuated thus as they traverse the subject H. Therefore, the unknown substances in the portion where the X-ray contrast medium is administered to the subject H (unknown substances in the thickness of the X-ray contrast medium) are just water and the X-ray contrast medium. Accordingly, the thickness is worked out by solving the system of equations obtained from formula 2 over two integration ranges. In the two integration ranges, X-ray absorption increases/decreases at energies above/below (before/after) the K-absorption edge of the X-ray contrast medium. Consequently, energy regions are selected above and below the K-absorption edge, and are set to predetermined energy ranges above and below the K-absorption edge of the X-ray contrast medium. In the case of an iodine contrast medium, for instance, the K-absorption edge of the iodine is 33.2 keV. Therefore, the two integration ranges are set to a predetermined energy range $\phi 1$ smaller than 33.2 keV, and a predetermined energy range $\phi 2$ greater than 33.2 keV. The predetermined energy range may be any arbitrary range, but sensitivity towards the presence or absence of X-ray contrast medium is lost if the energy range is too wide, while too narrow an energy range entails fewer X-rays within the energy range, which makes for poor statistical precision.

Thus, the thickness computing unit 132 can work out the thickness of the object to be inspected on the basis of a ratio $\Phi 1/\Phi 2$ of the number of transmitted X-rays within a predetermined energy range $\phi 1$ smaller than the K-absorption edge of the object to be inspected, and the number of transmitted X-rays within a predetermined energy range $\phi 2$ greater than the K-absorption edge of the object to be inspected. More specifically, the thickness computing unit 132 can work out the thickness of the object to be inspected based on a ratio between the integration value of the number of X-rays within an energy region corresponding to a predetermined energy range $\phi 1$ which is smaller than the K-absorption edge of the object to be inspected, and the integration value of the number of X-rays within an energy region corresponding to a predetermined energy range $\phi 2$ which is greater than the K-absorption edge of the object to be inspected.

As an example, in the case of CT measurement by filtered X-ray energy differences, the ratio $\Phi 1/\Phi 2$ is given by formula 3 below. Upon normalization of the results with respect to air in the region outside the object to be inspected, the ratio $\Phi 1/\Phi 2$ is given by formula 4 below.

$$\frac{\phi_1}{\phi_2} = \qquad (3)$$

$$\frac{\psi(E_1)}{\psi(E_2)} \exp\{-(\overline{\mu_I}(E_1) - \overline{\mu_I}(E_2)) \cdot t_I\} \cdot \exp\{-(\overline{\mu_W}(E_1) - \overline{\mu_W}(E_2)) \cdot t_W\}.$$

$$\ln \frac{\phi_1}{\phi_2} = 1 - (\overline{\mu_I}(E_1) - \overline{\mu_I}(E_2)) \cdot t_I - (\overline{\mu_W}(E_1) - \overline{\mu_W}(E_2)) \cdot t_W. \qquad (4)$$

In the formulas, $\psi(E_n)$ is the X-ray spectrum of energy $E_n$, the overbarred $\mu_I(E_n)$ and the overbarred $\mu_W(E_n)$ are the mean attenuation coefficients of iodine and water, respectively, for X-rays in the energy range $E_n$, and $t_I$ and $t_w$ are the thickness of the iodine and water, respectively.

The image reconstructing unit 133 of the processing unit 13 reconstructs the CT image (CT image data) of the subject H on the basis of the thickness of the object to be inspected as computed by the thickness computing unit 132, in accordance with a predetermined CT imaging method. For instance, the image reconstructing unit 133 uses, as projection data, the thickness of the object to be inspected, which is computed by the thickness computing unit 132, and performs convolution of the projection data and a predetermined reconstruction function. The image reconstructing unit 133 generates then a CT image (CT image data) of the subject H through back-projection of the convolution result. More specifically, current values are used as the projection data for generating the CT image when transmitted X-rays are measured in the form of current in a conventional measurement method. Instead of using current values, a CT image is generated in the present embodiment by using, as the projection data, a ratio $\Phi 1/\Phi 2$ between the number of transmitted X-rays in a predetermined energy range ϕ1 smaller than the K-absorption edge of the object to be inspected and the number of transmitted X-rays in a predetermined energy range ϕ2 greater than the K-absorption edge of the object to be inspected.

Once the CT image (CT image data) of the subject H is generated, the processing unit 13 optionally causes the CT image of the subject H to be displayed on the image display unit 16. The processing unit 13 optionally stores CT image data of the subject H in the image storing unit 14.

In the X-ray CT apparatus 1, thus, the thickness of the object to be inspected (for instance, an X-ray contrast medium) is computed based on the number of transmitted X-rays in specific energy ranges ϕ1, ϕ2, and the CT image of the subject H is reconstructed on the basis of the computed thickness of the object to be inspected. As a result, the X-ray CT apparatus according to the present embodiment allows obtaining a constant CT value for the thickness of the object to be inspected independently of the size of the subject H and of X-ray tube voltage (X-ray energy distribution), and allows thus generating stably X-ray CT images of the subject H. The X-ray CT apparatus 1, moreover, is substantially insensitive to beam hardening of the X-rays. This results in fewer artifacts, even during generation of CT images of substances having comparatively high X-ray absorption coefficients.

EXAMPLES AND COMPARATIVE EXAMPLES

Examples and comparative examples of the present invention are explained next.

Figure 2:
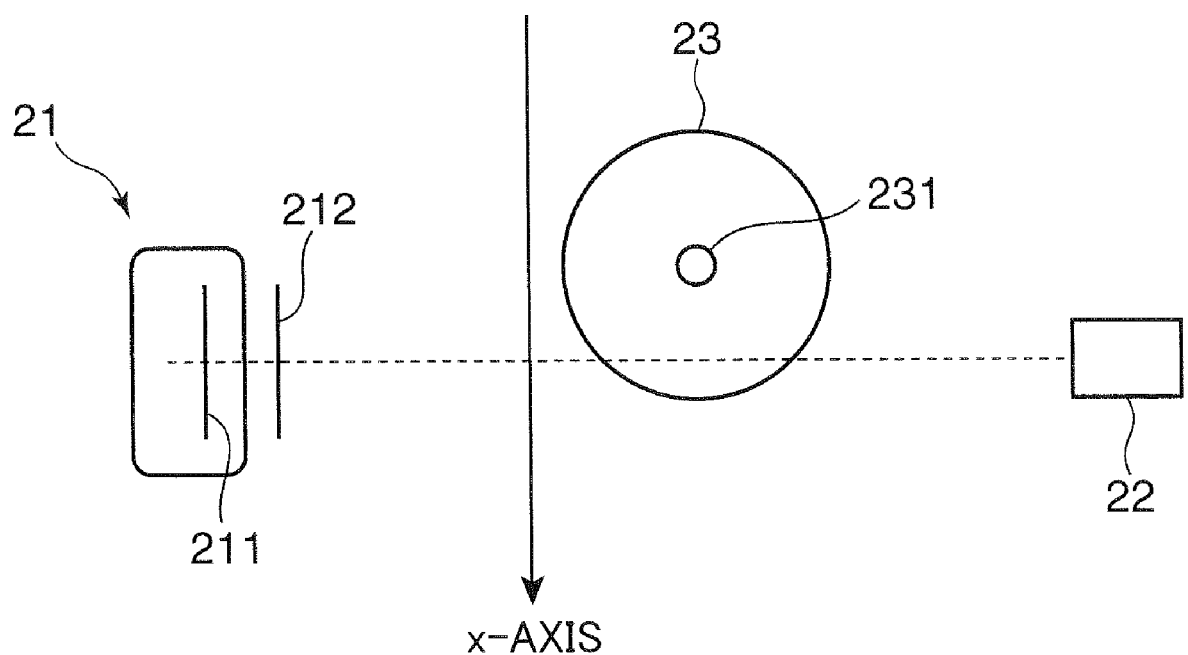
FIG. 2 is a diagram illustrating the configuration in an example of the embodiment.

FIG. 2 is a diagram illustrating the configuration of an example of the above embodiment. The present example was carried out on the basis of simulation calculations. The configuration of the present example comprises, as shown in FIG. 2, an X-ray irradiating unit 21 that irradiates X-rays, an X-ray measuring unit 22 that measures X-rays, and a water phantom that mimics a living organism. The water phantom 23 is shaped as a solid cylinder of predetermined diameter length, and has formed in the center thereof a 1 cm-diameter iodine region 231. The interior of the iodine region 231 is filled with iodine, as a contrast medium, at various concentrations. The water phantom 23 moves along a straight line that is perpendicular to the straight line that joins the X-ray irradiating unit 21 and the X-ray measuring unit 22. The straight line perpendicular to the straight line that joins the X-ray irradiating unit 21 and the X-ray measuring unit 22 is taken as the x-axis. The X-ray irradiating unit 21 irradiates X-rays (filtered X-rays) that pass through an aluminum filter 211 having a thickness of 2 mm, according to the Pharmaceutical Affairs Act, and passes then through a lanthanum filter 212 having a thickness of 100 μm.

Figure 3A:
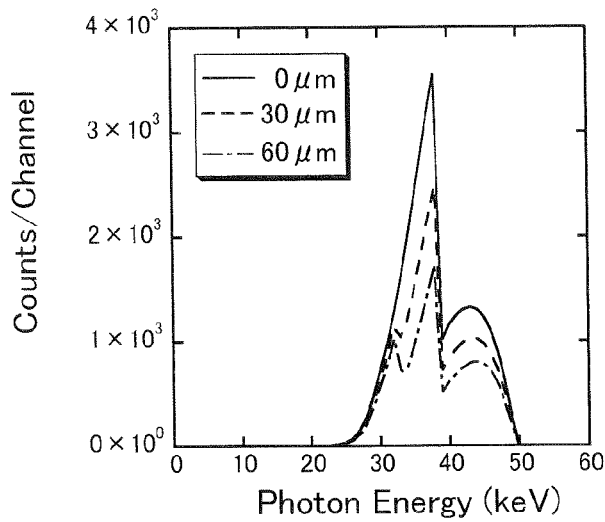
FIG. 3 is a diagram illustrating an energy spectrum of transmitted X-rays upon changes in iodine thickness and X-ray tube voltage in an example.
Figure 3B:
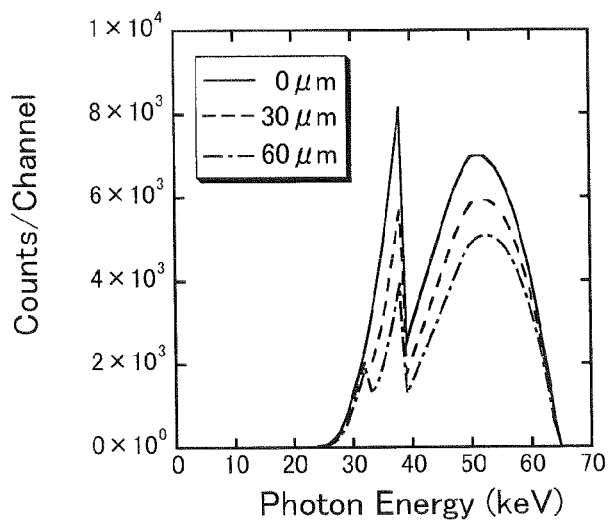
Figure 3C:
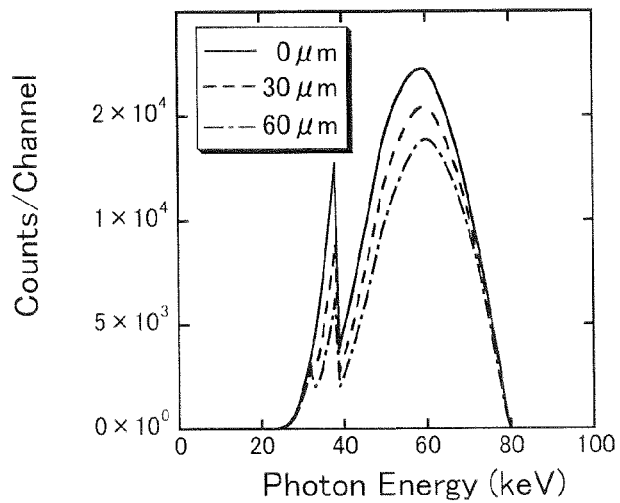

FIG. 3 is a diagram illustrating an energy spectrum of the transmitted X-rays upon changes in the iodine thickness and X-ray tube voltage in the example. In FIG. 3, the horizontal axis represents photon energy expressed in keV units, and the vertical axis represents the count number of X-rays detected by an X-ray measuring unit. The solid line in FIG. 3 denotes a case where iodine thickness is 0 μm (water), the broken line denotes a case where iodine thickness is 30 μm, and the dotted-dashed line denotes a case where iodine thickness is 60 μm. The iodine thickness is a value that results from calculating the amount of iodine per cm of water in the X-ray propagation direction, on the basis of the concentration of iodine mixed into water. FIGS. 3(A), (B) and (C) illustrate instances where the X-ray tube voltage of the X-ray tube (not shown) in the X-ray irradiating unit 21 is 50 kV, 65 kV and 80 kV, respectively. Therefore, the X-rays irradiated by the X-ray irradiating unit 21 onto the water phantom 23 have increasing high-energy components in the order of FIGS. 3(A), (B) and (C).

The count number at substantially the K-absorption edge of iodine does not drop, obviously, when the iodine thickness is 0 μm, as can be seen in FIGS. 3(A), (B) and (C). When the iodine thickness is 30 μm and 60 μm, there is observed a drop in the count number at substantially the K-absorption edge of iodine. The drop is greater for iodine thickness 60 μm than for iodine thickness 30 μm.

Figure 4A:
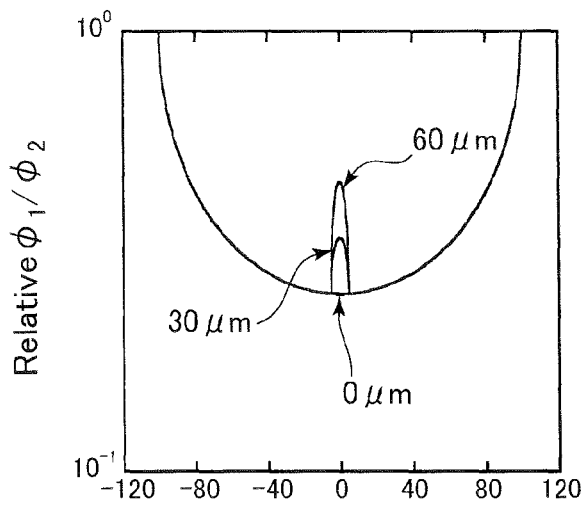
FIG. 4 is a diagram illustrating a count ratio of $\Phi1/\Phi2$ of transmitted X-rays through a 20 cm-diameter water phantom, upon changes in X-ray tube voltage, in an example.
Figure 4B:
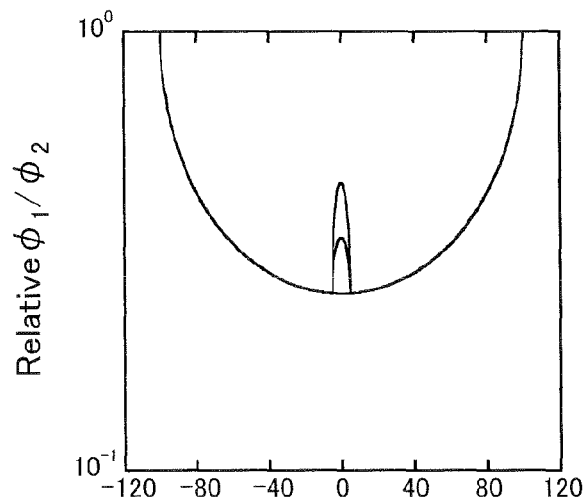
Figure 4C:
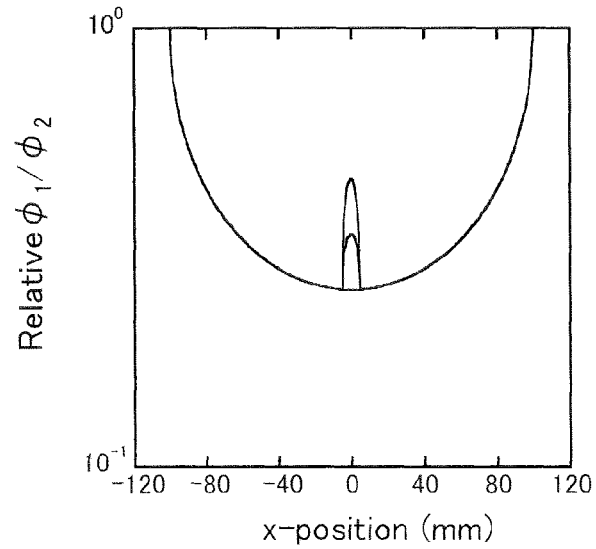
Figure 5A:
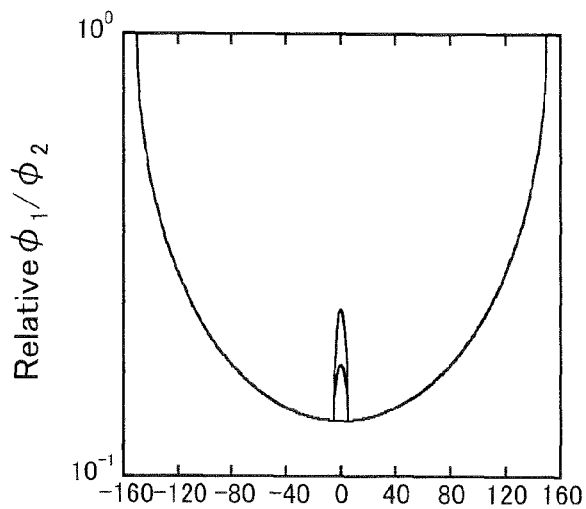
FIG. 5 is a diagram illustrating a count ratio Φ1/Φ2 of transmitted X-rays through a 30 cm-diameter water phantom, upon changes in X-ray tube voltage, in an example.
Figure 5B:
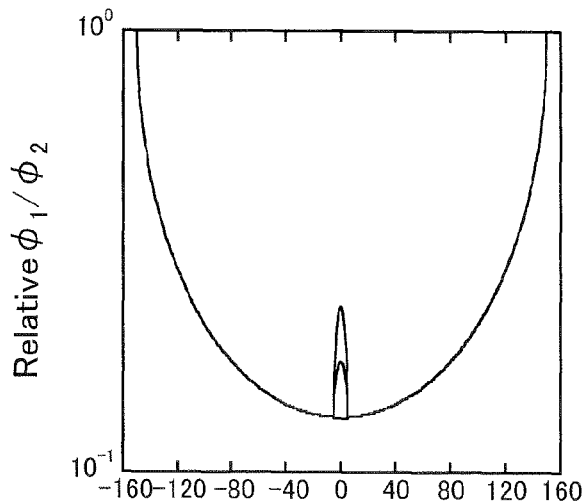
Figure 5C:
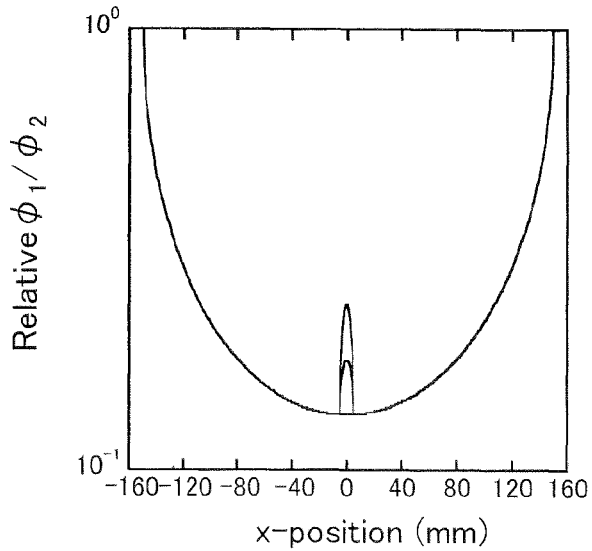

FIGS. 4 and 5 are diagrams illustrating the change in the count ratio Φ1/Φ2 of transmitted X-rays upon changes in X-ray tube voltage in the example. In the figure, Φ1 is the count number within an energy range from 27.4 keV to 33.2 keV, smaller than the K-absorption edge 33.2 keV of iodine. In the figure, Φ2 is the count number within an energy range from 33.2 keV to 38.9 keV, greater than the K-absorption edge 33.2 keV of iodine. The horizontal axis in FIGS. 4 and 5 represents position along the x-axis, expressed in mm units, and the vertical axis represents the count ratio Φ1/Φ2, expressed logarithmically. The origin of coordinates of the x-axis is the intersection between the x-axis and the straight line that joins the X-ray irradiating unit 21 and the X-ray measuring unit 22, and the center of the water phantom 23 is at the origin of coordinates of the x-axis. FIG. 4 illustrates an instance where the diameter of the water phantom 23 is 20 cm, and FIG. 5 illustrates an instance where the diameter of the water phantom is 30 cm. FIG. 4(A) and FIG. 5(A) illustrate an instance where the X-ray tube voltage of the X-ray irradiating unit 21 is 50 kV, FIG. 4(B) and FIG. 5(B) illustrate an instance where the X-ray tube voltage of the X-ray irradiating unit 21 is 65 kV, and FIG. 4(C) and FIG. 5(C) illustrate an instance where the X-ray tube voltage of the X-ray irradiating unit 21 is 80 kV.

As described above, the iodine thickness of the iodine region 231 in the water phantom 23 is calculated based on the count ratio Φ1/Φ2, to generate an X-ray CT image of the iodine region 231.

A comparison between FIGS. 4(A) to (C) reveals that the count ratio Φ1/Φ2 does not depend on the X-ray tube voltage of the X-ray irradiating unit 21. That is, the count ratio Φ1/Φ2 does not depend on the energy distribution of the X-rays that are irradiated by the X-ray irradiating unit 21 towards the water phantom 23. The figures show also that absorption by iodine (iodine contrast medium) logarithmically expressed is directly proportional to the iodine thickness. That is, absorption by iodine logarithmically expressed is roughly double when the iodine thickness is 60 μm than when the iodine thickness is 30 μm. The above finding is also borne out upon comparison between FIGS. 5 (A) to (C).

Likewise, comparison between FIGS. 4 and 5 reveals that changes in the logarithmically-expressed count ratio Φ1/Φ2 are proportional to changes in iodine thickness.

Figure 6:
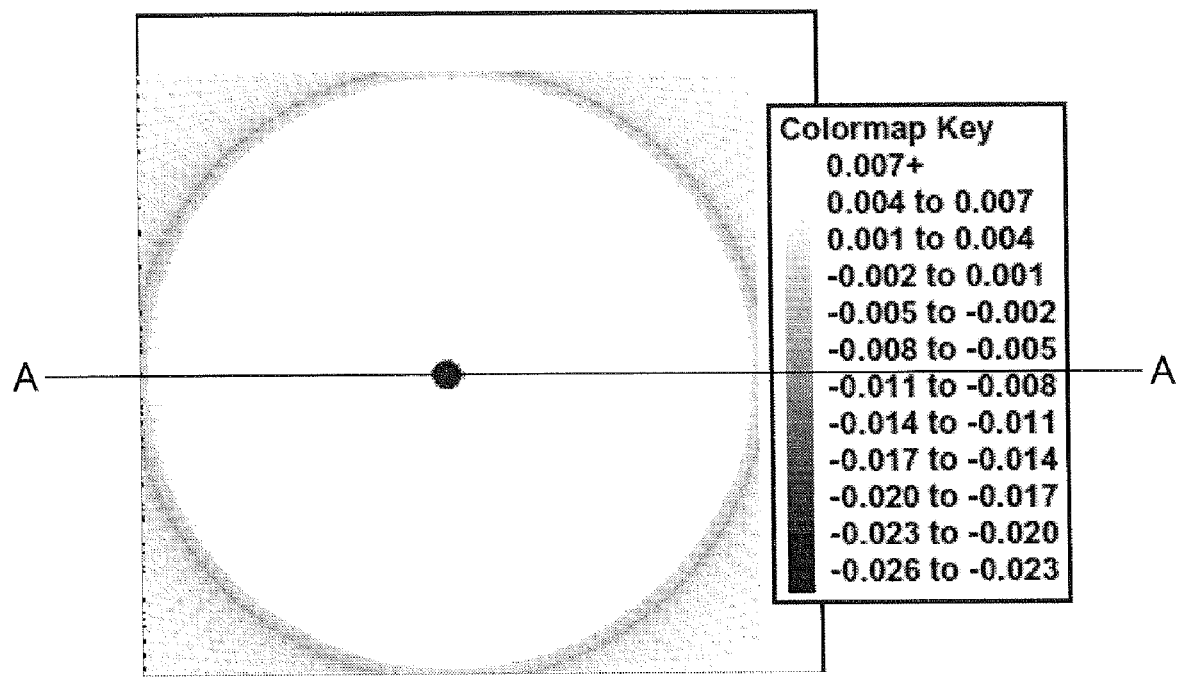
FIG. 6 is a diagram illustrating an X-ray CT image of a water phantom based on measurement values in an example.
Figure 7A:
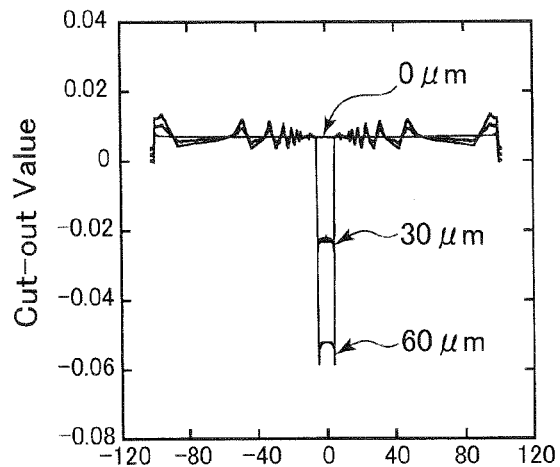
FIG. 7 is a diagram illustrating CT values along a straight line (AA line in FIG. 6) that extends in a radial direction and traverses the center of a water phantom (diameter 20 cm) in an example.
Figure 7B:
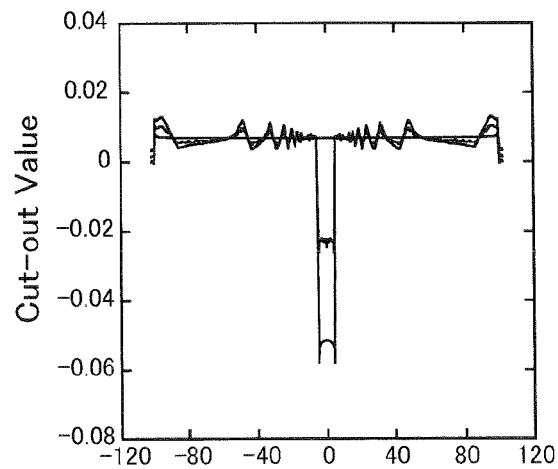
Figure 7C:
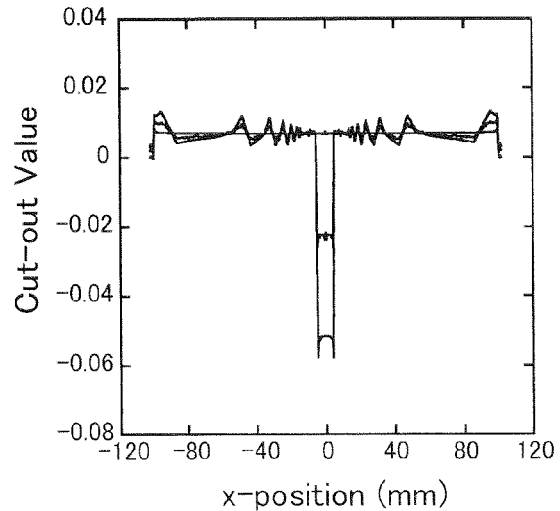
Figure 8A:
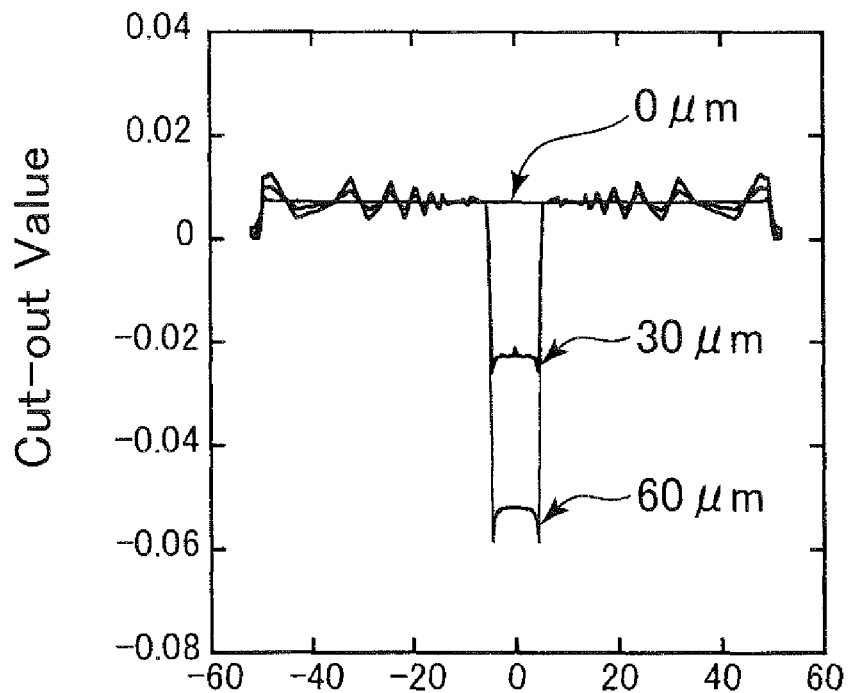
FIG. 8 is a diagram illustrating CT values along a straight line (AA line in FIG. 6) that extends in a radial direction and traverses the center of a water phantom (diameter 10 cm, 30 cm) in an example.
Figure 8B:
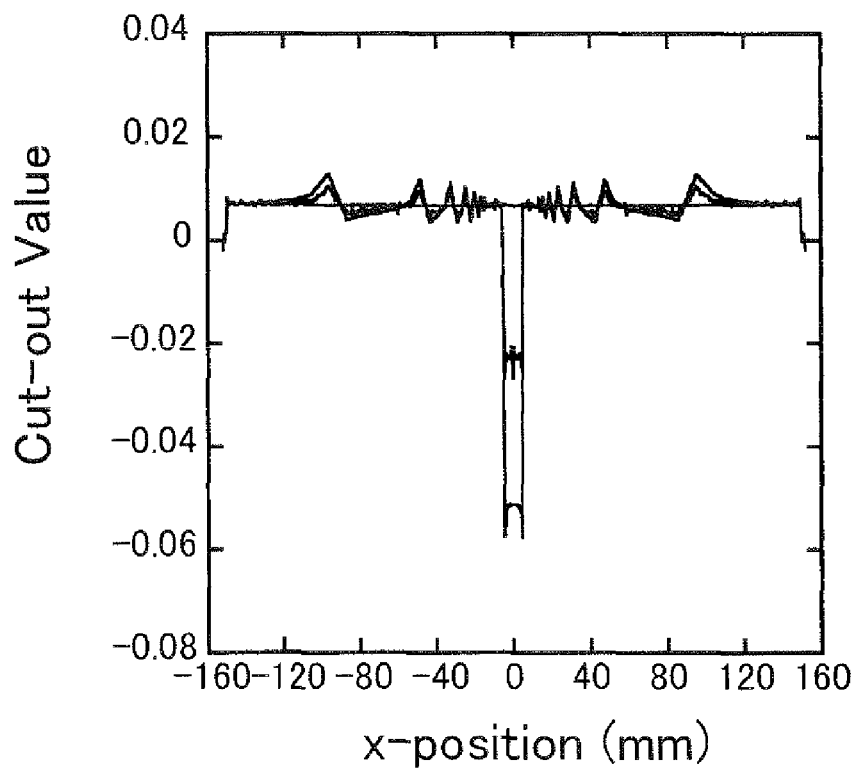

FIG. 6 is a diagram illustrating an X-ray CT image of a water phantom based on measurement values in the example. In FIG. 6, iodine thickness increases as the color changes from white to black. FIGS. 7 and 8 are diagrams illustrating CT values along a straight line (line AA in FIG. 6), in the radial direction, that traverses the water phantom of the example. The horizontal axis in FIGS. 7 and 8 represents position along the x-axis, expressed in mm units. The vertical axis is the CT value. FIGS. 7(A), (B) and (C) illustrate instances where the X-ray tube voltage of the X-ray tube (not shown) in the X-ray irradiating unit 21 is 50 kV, 65 kV and 80 kV, respectively. FIG. 7 illustrates an instance where the diameter of the water phantom 23 is 20 cm, and FIGS. 8(A)

and (B) illustrate instances where the X-ray tube voltage is 65 kV and the diameter of the water phantom 23 is 10 cm and 30 cm, respectively.

As FIGS. 6 to 8 show, the CT value does not depend on the X-ray tube voltage of the X-ray irradiating unit 21 or on the size of the water phantom 23. Therefore, the contrast medium can be imaged under conditions where X-ray beam hardening is immaterial to the X-ray CT image generated on the basis of the count ratio $\Phi 1/\Phi 2$.

On the other hand, the current value depends both on the X-ray tube voltage of the X-ray irradiating unit 21 and on the size of the water phantom 23 when an X-ray CT image is formed on the basis of changes in currents that derive from transmitted X-rays in a conventional measurement method, as in a below-described comparative example illustrated in FIGS. 9 and 10. By contrast, the count ratio $\Phi 1/\Phi 2$ does not depend on the X-ray tube voltage of the X-ray irradiating unit 21 or on the size of the water phantom 23 when the X-ray CT image is formed on the basis of the number of transmitted X-rays, as described above. The current value depends both on the X-ray tube voltage of the X-ray irradiating unit 21 and on the size of the water phantom 23 when an X-ray CT image is formed on the basis of changes in the dose of transmitted X-rays as in a below-described comparative example illustrated in FIGS. 11 to 13. By contrast, the CT value does not depend on the X-ray tube voltage of the X-ray irradiating unit 21 or on the size of the water phantom 23 when the X-ray CT image is formed based on the number of transmitted X-rays. Therefore, forming an X-ray CT image based on the number of transmitted X-rays is superior to forming an X-ray CT image on the basis of changes in the dose i.e. in the current values, of the transmitted X-rays.

The example explained above describes results when using iodine as the contrast medium, but the same effect is obtained using other contrast media, such as barium contras media, gold contrast media and the like. The K-absorption edge of barium is 37.4 keV. The K-absorption edge of gold is 80.7 keV. Gold contrast media are disclosed in, for instance, "J F HAINFELD, D N SLATKIN, T M FOCELLA and H M SMILOWITZ," Gold nanoparticles: a new X-ray contrast agent", The British Journal of Radiology, 79 (2006), 248-253".

An explanation follows next on an instance, as a comparative example, of formation of an X-ray CT image on the basis of changes in the dose of transmitted X-rays in the configuration illustrated in FIG. 2.

Figure 9A:
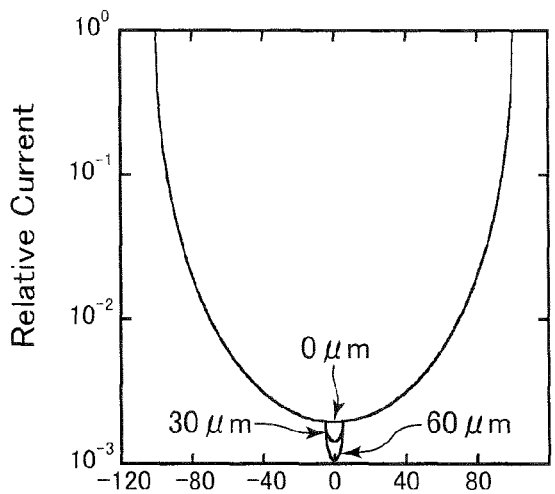
FIG. 9 is a diagram illustrating measurement results of transmitted X-rays, measured as current, through a 20 cm-diameter water phantom, upon changes in X-ray tube voltage, in a comparative example.
Figure 9B:
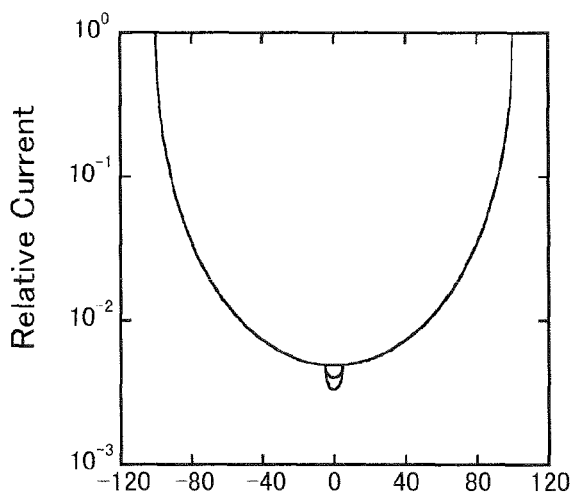
Figure 9C:
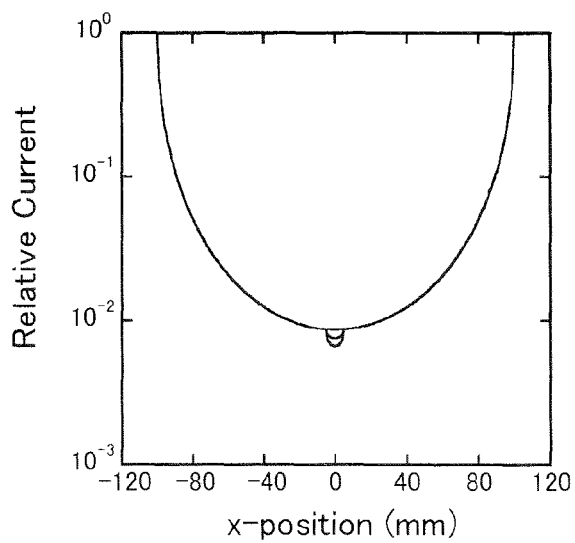
Figure 10A:
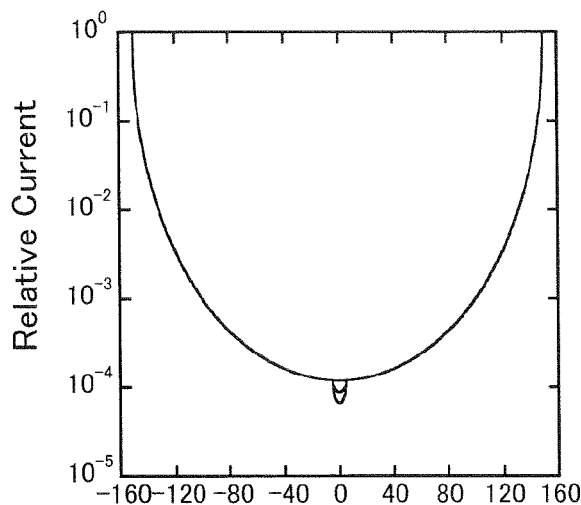
FIG. 10 is a diagram illustrating measurement results of transmitted X-rays, measured as current, through a 30 cm-diameter water phantom, upon changes in X-ray tube voltage, in a comparative example.
Figure 10B:
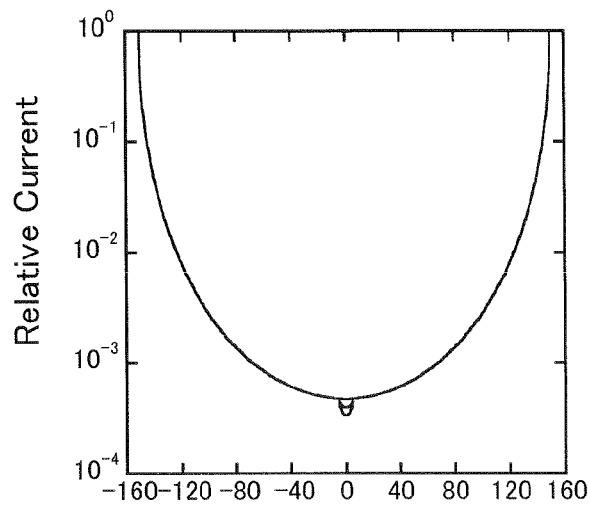
Figure 10C:
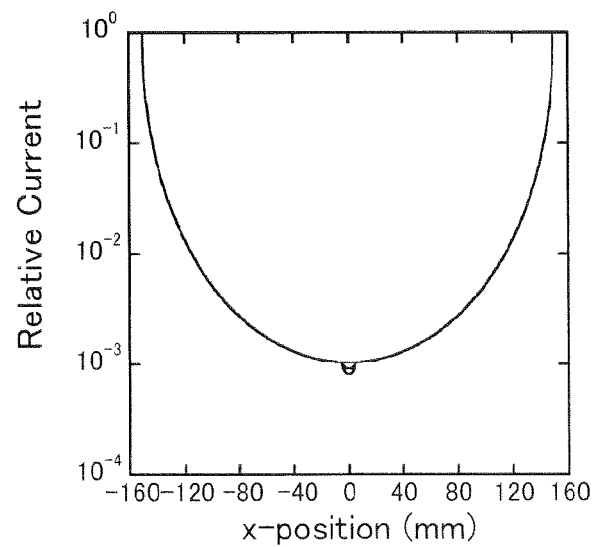

FIGS. 9 and 10 are diagrams illustrating results of measurement of transmitted X-rays, as electric current, upon changes of X-ray tube voltage, in a comparative example. The horizontal axis in FIGS. 9 and 10 represents position along the x-axis, expressed in mm units. The vertical axis represents current values expressed logarithmically. The origin of coordinates of the x-axis is the intersection between the x-axis and the straight line that joins the X-ray irradiating unit 21 and the X-ray measuring unit 22, such that the center of the water phantom 23 coincides with the coordinate origin of the x-axis. FIG. 9 illustrates an instance where the diameter of the water phantom 23 is 20 cm, and FIG. 10 illustrates an instance where the diameter of the water phantom is 30 cm. FIGS. 9(A) and 10(A) illustrate an instance where the X-ray tube voltage of the X-ray irradiating unit 21 is 50 kV, FIGS. 9(B) and 10(B) illustrate an instance where the X-ray tube voltage of the X-ray irradiating unit 21 is 65 kV, and FIGS. 9(C) and 10(C) illustrate an instance where the X-ray tube voltage of the X-ray irradiating unit 21 is 80 kV.

FIGS. 9 and 10 correspond respectively to FIGS. 4 and 5. As the comparative examples of FIGS. 9(A) to (C) show, the change in current value decreases as the X-ray tube voltage of the X-ray irradiating unit 21 becomes higher. This indicates that the current value depends on the X-ray tube voltage of the X-ray irradiating unit 21. Specifically, the current value depends on the energy distribution of the X-rays irradiated by the X-ray irradiating unit 21 towards the water phantom 23. The above finding is also borne out upon comparison between FIGS. 10 (A) to (C).

As a comparison between FIGS. 9 and 10 reveals, the change in current value becomes smaller as the size of the water phantom 23 increases. The current value depends thus on the size of the water phantom 23.

Figure 11:
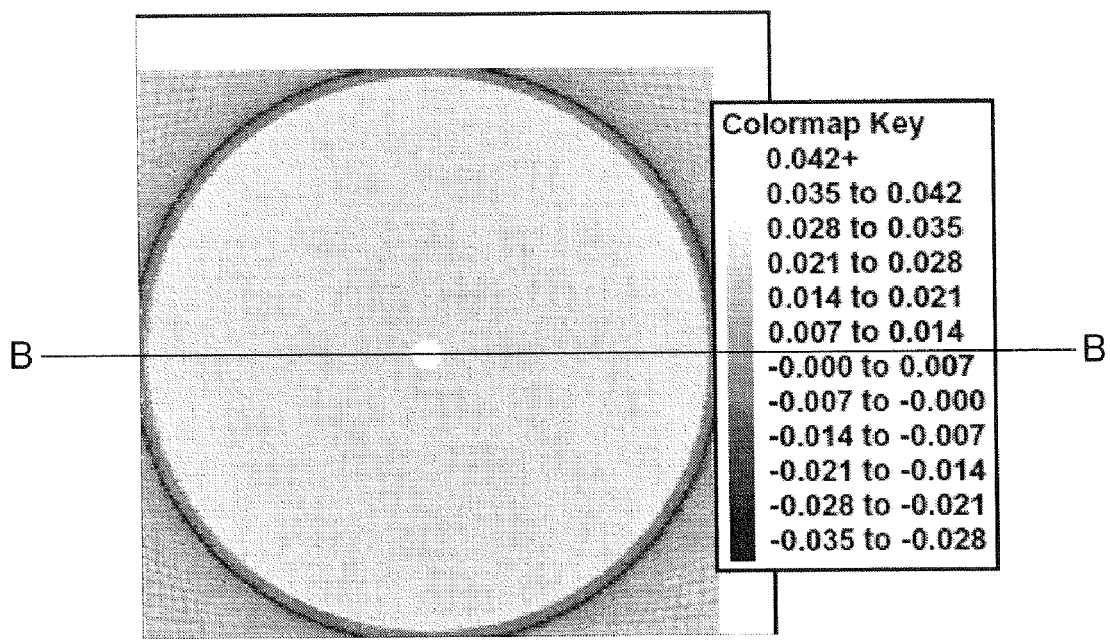
FIG. 11 is a diagram illustrating an X-ray CT image of a water phantom based on measurement values in a comparative example.
Figure 12A:
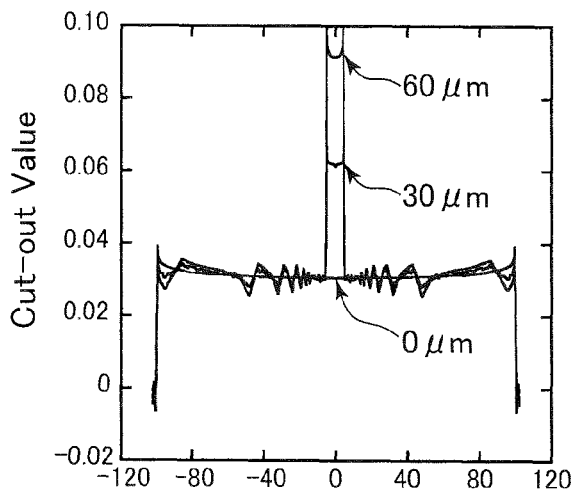
FIG. 12 is a diagram illustrating CT values along a straight line (BB line in FIG. 11) that extends in a radial direction and traverses the center of a water phantom (diameter 20 cm) in a comparative example.
Figure 12B:
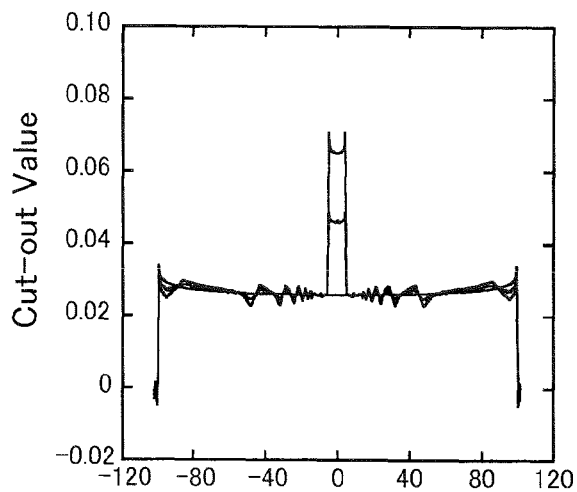
Figure 12C:
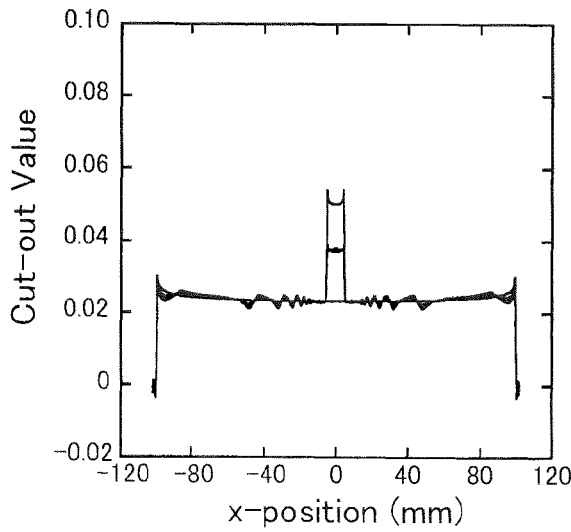
Figure 13A:
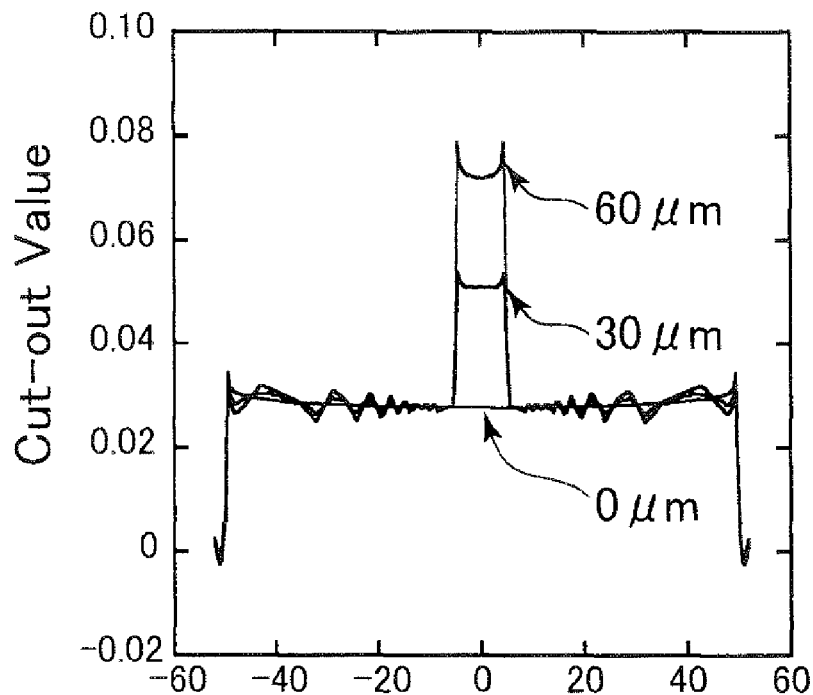
FIG. 13 is a diagram illustrating CT values along a straight line (BB line in FIG. 11) that extends in a radial direction and traverses the center of a water phantom (diameter 10 cm, 30 cm) in a comparative example.
Figure 13B:
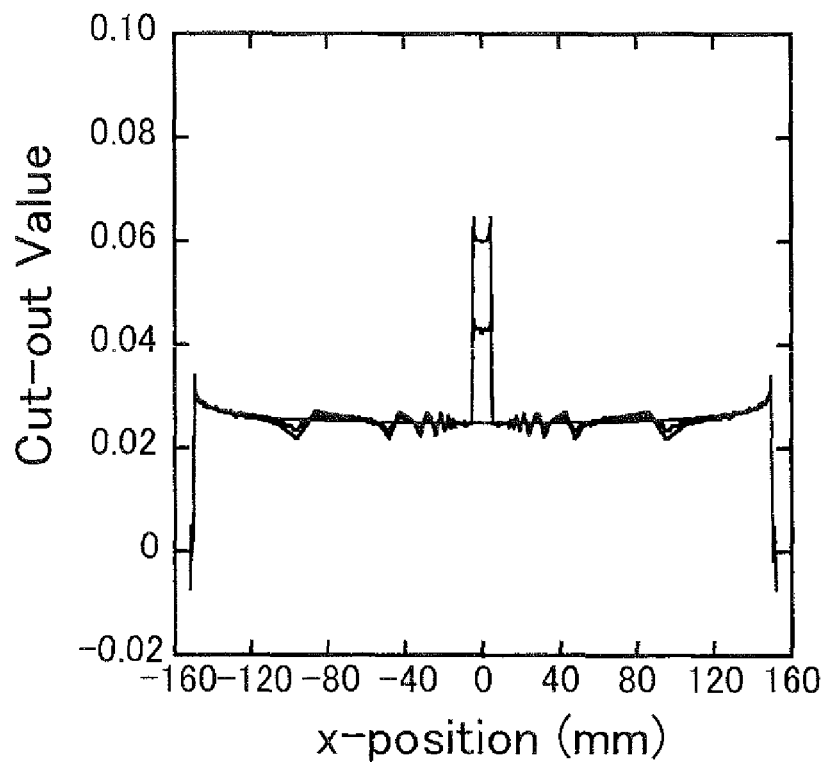

FIG. 11 is a diagram illustrating an X-ray CT image of a water phantom based on measurement values in a comparative example. In FIG. 11, the iodine thickness increases as the color changes from black to white. FIGS. 12 and 13 are diagrams illustrating CT values along a straight line (line BB in FIG. 11), in the radial direction, that traverses the water phantom of the comparative example. The horizontal axis in FIGS. 12 and 13 represents position along the horizontal (X) axis, expressed in mm units. The vertical axis is the CT value. FIGS. 12(A), (B) and (C) illustrate instances where the X-ray tube voltage of the X-ray tube (not shown) in the X-ray irradiating unit 21 is 50 kV, 65 kV and 80 kV, respectively. FIG. 12 illustrates an instance where the diameter of the water phantom 23 is 20 cm, and FIGS. 13(A) and (B) illustrate instances where the X-ray tube voltage is 65 kV and the diameter of the water phantom 23 is 10 cm and 30 cm, respectively.

As FIGS. 11 to 13 show, the CT value depends on the X-ray tube voltage of the X-ray irradiating unit 21 and also on the size of the water phantom 23.

The present description discloses various technical aspects, the main technical features whereof are summarized below.

In one aspect, an X-ray CT apparatus comprises an X-ray irradiating unit that irradiates X-rays onto a subject; an X-ray measuring unit that opposes the X-ray irradiating unit across the subject and measures the number of transmitted X-rays within a specific energy range that corresponds to an object to be inspected inside the subject, from among the transmitted X-rays that pass through the subject; a thickness computing unit that computes the thickness of the object to be inspected on the basis of the number of the transmitted X-rays measured by the X-ray measuring unit; and an image reconstructing unit that reconstructs a CT image on the basis of the thickness of the object to be inspected as computed by the thickness computing unit. An X-ray CT method in another aspect comprises an X-ray irradiation step of irradiating X-rays onto a subject; an X-ray measurement step of measuring the number of transmitted X-rays within a specific energy range that corresponds to an object to be inspected inside the subject, from among the transmitted X-rays that pass through the subject; a thickness computing step of computing the thickness of the object to be inspected on the basis of the number of the transmitted X-rays measured by the X-ray measuring step; and an image reconstruction step of reconstructing a CT image on the basis of the thickness of the object to be inspected as computed in the thickness computing step.

In such an X-ray CT apparatus and X-ray CT method, the thickness of an object to be inspected is computed on the basis of the number of transmitted X-rays in the above specific energy range, and a CT image is reconstructed on the basis of the computed thickness of the object to be inspected. In the X-ray CT apparatus and X-ray CT method according to the present invention, therefore, an X-ray CT image can be generated stably and independently of the size of a subject and of X-ray tube voltage (X-ray energy distribution). The X-ray contrast medium may be a conventionally developed contrast medium.

In another aspect of the above X-ray CT apparatus, the object to be inspected is preferably an X-ray contrast medium, and the specific energy range is set above and below the K-absorption edge of the X-ray contrast medium.

In the above configuration, a specific energy range is set above and below the K-absorption edge (before and after the K-absorption edge) of the X-ray contrast medium. Therefore, the X-ray contrast medium in the subject is analyzed quantitatively, so that there can be generated a sharper X-ray CT image.

In another aspect of the above-described X-ray CT apparatus, preferably, the thickness computing unit computes the thickness of the object to be inspected on the basis of a ratio between the number of transmitted X-rays within a predetermined energy range that is smaller than the K-absorption edge of the object to be inspected, and the number of transmitted X-rays within a predetermined energy range that is greater than the K-absorption edge of the object to be inspected.

Such a configuration allows computing more adequately the thickness of the object to be inspected.

In another aspect of the above-described X-ray CT apparatus, preferably, the X-ray measuring unit comprises a detection medium that generates charge on account of energy imparted by transmitted X-rays that pass through the subject; and a plurality of electrodes disposed in the detection medium at positions removed by mutually different distances from an incidence end of the transmitted X-rays on the detection medium.

In another aspect of the above-described X-ray CT apparatus, preferably, the X-ray measuring unit comprises a plurality of detection media arrayed in a propagation direction of the transmitted X-rays that pass through the subject, such that charge is generated at each of the detection media on account of energy imparted by the transmitted X-rays, and the detection media act as absorption bodies of the transmitted X-rays, as a result of which there varies the thickness of the absorption bodies through which the transmitted X-rays pass before arriving at the respective detection media. The above plurality of detection media may comprise each the same material or dissimilar materials. The X-ray measuring unit affords appropriate results by using, in particular, detection media having dissimilar materials.

The above configuration allows measuring the number of transmitted X-rays in a specific energy range in accordance with the object to be inspected inside the subject, from among the X-rays that pass through the subject, and allows drawing thereupon a CT image, at the same processing speed as in the case of an X-ray CT apparatus that relies on current measurements. The above configuration provides therefore a practical X-ray CT apparatus.

In another aspect of the above-described X-ray CT apparatus, preferably, the X-ray contrast medium is any from among an iodine contrast medium, a barium contrast medium and a gold contrast medium.

When in the above configuration the X-ray contrast medium is an iodine contrast medium, the blood vessels of the subject are imaged and there is generated a CT image of the imaged blood vessels of the subject. Iodine contrast media are suitable for blood flow observation. Iodine contrast media highlight, for instance, tissues comparatively rich in vasculature, and the are suitable for diagnosing tumors such as cancer. When the X-ray contrast medium is a barium contrast medium there can be imaged the digestive system of the subject, to generate a CT image of the imaged digestive system of the subject. When the X-ray contrast medium is a gold contrast medium there can be imaged cancerous tissues in the subject, to generate a CT image of the imaged cancerous tissues in the subject, since gold contrast media accumulate in cancerous tissue.

In another aspect of the above-described X-ray CT apparatus, preferably, the X-ray irradiating unit irradiates filtered X-rays, resulting from filtering X-rays through a filter, onto the subject.

In the above configuration, some of the X-rays are cut by the filter, and hence subject exposure can be reduced.

This application is based upon Japanese Patent Application No. 2007-211948, filed on 15 Aug. 2007, the entire contents of which are incorporated herein by reference.

To disclose the present invention, the latter has been appropriately and sufficiently explained by means of the above-described embodiments with reference to accompanying drawings. However, a person skilled in the art will easily appreciate that the above-described embodiments can be modified and/or improved in various ways. Unless departing from the scope of the appended claims, therefore, such modifications and improvements that a person skilled in the art could realize are meant to lie within the scope of the claims.

The invention claimed is:

1. An X-ray CT apparatus, comprising:
an X-ray irradiating unit that irradiates X-rays onto a subject;
an X-ray measuring unit that opposes said X-ray irradiating unit across said subject and measures the number of transmitted X-rays within a specific energy range that corresponds to an object to be inspected inside said subject, from among the transmitted X-rays that pass through said subject;
a thickness computing unit that computes the thickness of said object to be inspected on the basis of the number of said transmitted X-rays measured by said X-ray measuring unit; and
an image reconstructing unit that reconstructs a CT image on the basis of the thickness of said object to be inspected as computed by said thickness computing unit,
wherein said object to be inspected is an X-ray contrast medium,
said specific energy range is set above and below the K-absorption edge of said X-ray contrast medium,
said thickness computing unit obtains the thickness $t_I$ of said object to be inspected on the basis of a ratio $\Phi_1/\Phi_2$ between the number of transmitted X-rays within a predetermined energy range $\Phi_1$ that is smaller than the K-absorption edge of said object to be inspected, and the number of transmitted X-rays within a predetermined energy range $\Phi_2$ that is greater than the K-absorption edge of said object to be inspected,
said image reconstructing unit uses, as projection data, the thickness of said object to be inspected which is computed by said thickness computing unit, performs convolution of said projection data and a predetermined reconstruction function, and generates a CT image of said subject through back projection of the convolution result,
the ratio $\Phi_1/\Phi_2$ being given by the following formula:

$$\ln\frac{\phi_1}{\phi_2} = 1 - (\overline{\mu_I}(E_1) - \overline{\mu_I}(E_2)) \cdot t_I - (\overline{\mu_W}(E_1) - \overline{\mu_W}(E_2)) \cdot t_W.$$

wherein overbarred $\mu_I(E_n)$ and overbarred $\mu_W(E_n)$ are the mean attenuation coefficients of said object to be inspected and water, respectively, for X-rays of an energy range $E_n$ (n=1, 2), and $t_I$ and $t_w$ are the thickness of said object to be inspected and water, respectively.

2. The X-ray CT apparatus according to claim 1, wherein said X-ray measuring unit comprises a detection medium that generates charge on account of energy imparted by transmitted X-rays that pass through said subject; and a plurality of electrodes disposed in said detection medium at positions removed by mutually different distances from an incidence end of said transmitted X-rays on said detection medium.

3. The X-ray CT apparatus according to claim 1, wherein said X-ray measuring unit comprises a plurality of detection media arrayed in a propagation direction of said transmitted X-rays that pass through said subject, such that charge is generated at each of said detection media on account of energy imparted by said transmitted X-rays, and said detection media act as absorption bodies of said transmitted X-rays, as a result of which there varies the thickness of the absorption bodies through which said transmitted X-rays pass before arriving at said respective detection media.

4. The X-ray CT apparatus according to claim 1, wherein said X-ray contrast medium is any from among an iodine contrast medium, a barium contrast medium and a gold contrast medium.

5. The X-ray CT apparatus according to claim 1, wherein said X-ray irradiating unit irradiates filtered X-rays, resulting from filtering X-rays through a filter, onto the subject.

6. An X-ray CT method, comprising:
an X-ray irradiation step of irradiating X-rays onto a subject excluding a living organism;
an X-ray measurement step of measuring the number of transmitted X-rays within a specific energy range that corresponds to an object to be inspected inside said subject, from among the transmitted X-rays that pass through said subject;
a thickness computing step of computing the thickness of said object to be inspected on the basis of the number of said transmitted X-rays measured by said X-ray measuring step; and
an image reconstruction step of reconstructing a CT image on the basis of the thickness of said object to be inspected as computed in said thickness computing step,
wherein said object to be inspected is an X-ray contrast medium,
said specific energy range is set above and below the K-absorption edge of said X-ray contrast medium,
in said thickness computing step, the thickness $t_I$ of said object to be inspected is obtained on the basis of a ratio $\Phi1/\Phi2$ between the number of transmitted X-rays within a predetermined energy range $\Phi1$ that is smaller than the K-absorption edge of said object to be inspected, and the number of transmitted X-rays within a predetermined energy range $\Phi2$ that is greater than the K-absorption edge of said object to be inspected,
in said image reconstruction step, the thickness of said object to be inspected, which is computed in said thickness computing step, is used as projection data, said projection data and a predetermined reconstruction function are convoluted, and a CT image of said subject is generated through back projection of the convolution result,
the ratio $\Phi1/\Phi2$ being given by the following formula:

$$\ln\frac{\phi_1}{\phi_2} = 1 - (\overline{\mu_I}(E_1) - \overline{\mu_I}(E_2))\cdot t_I - (\overline{\mu_W}(E_1) - \overline{\mu_W}(E_2))\cdot t_W.$$

wherein overbarred $\mu_I(E_n)$ and overbarred $\mu_W(E_n)$ are the mean attenuation coefficients of said object to be inspected and water, respectively, for X-rays of an energy range $E_n$ (n=1, 2), and $t_I$ and $t_w$ are the thickness of said object to be inspected and water, respectively.

* * * * *